United States Patent [19]

Lovell et al.

[11] Patent Number: 5,567,591
[45] Date of Patent: *Oct. 22, 1996

[54] AMPLIFIED ASSAY FOR ANALYTE

[75] Inventors: Stephen J. Lovell, Towson; Jeffrey H. Bruton, Randallstown, both of Md.

[73] Assignee: Becton Dickinson and Company, Franklin Lakes, N.J.

[*] Notice: The term of this patent shall not extend beyond the expiration date of Pat. No. 5,369,036.

[21] Appl. No.: 289,833

[22] Filed: Aug. 12, 1994

Related U.S. Application Data

[63] Continuation of Ser. No. 719,488, Jun. 24, 1991, abandoned.
[51] Int. Cl.$^6$ .................................................. G01N 33/538
[52] U.S. Cl. ..................... 435/7.5; 435/7.95; 435/810; 435/969; 436/518; 436/528; 436/541; 436/829
[58] Field of Search ..................................... 435/7.5, 7.95, 435/810, 969; 436/518, 528, 541, 829

[56] References Cited

U.S. PATENT DOCUMENTS

| | | | |
|---|---|---|---|
| 4,193,983 | 3/1980 | Ullman et al. | 424/12 |
| 4,762,915 | 8/1988 | Kung et al. | 530/405 |
| 4,920,046 | 4/1990 | McFarland et al. | 435/7 |
| 5,369,036 | 11/1994 | Mercolino | 436/523 |

*Primary Examiner*—James C. Housel
*Assistant Examiner*—Christopher L. Chin
*Attorney, Agent, or Firm*—Bruce S. Weintraub

[57] ABSTRACT

An indirect assay for analyte employs a particle derivatized with a plurality of molecules of one or more compounds to increase assay sensitivity. In an indirect sandwich assay format, at least one of the compounds is a binder for the analyte, and the tracer is comprised of a binder for at least one of the compounds on the particle. In this manner, a plurality of tracer molecules may be indirectly bound to a single analyte molecule which is bound in a complex formed in the assay.

33 Claims, No Drawings

AMPLIFIED ASSAY FOR ANALYTE

This application is a continuation of application Ser. No. 07/719,488 filed on Jun. 24, 1991, now abandoned.

This invention relates to an assay for a ligand to be determined (analyte), and to products used in such assay. More particularly, the present invention relates to an indirect assay for determining analyte.

French Patent 2,523,311 discloses an indirect assay for determining analyte by either an indirect sandwich assay technique or an indirect competition assay technique.

In the indirect sandwich assay technique, there is formed a complex of binder for the analyte; analyte bound to the binder; a coupled compound comprising a binder for the analyte and albumin bound to the analyte; and a tracer comprised of anti-albumin which includes a label such as an enzyme, radioactive material, or fluorchrome.

In the indirect competitive assay technique, analyte and a coupled compound comprised of a ligand which is bound by the binder for the analyte and albumin compete for binding sites on a binder. In the assay, the tracer is comprised of labeled anti-albumin, whereby there is formed in the assay a complex of binder for the analyte; coupled compound bound to the binder; and tracer bound to the coupled compound.

The present invention is directed to improving such indirect assay techniques.

In accordance with one aspect of the present invention, there is provided an improvement in an indirect assay technique, which is either an indirect sandwich assay or an indirect competition assay, wherein, in the assay, a particle is derivatized with a plurality of molecules of one or more appropriate compounds, whereby a plurality of tracer molecules may be indirectly bound to the binder used in the assay through compounds on the particle.

More particularly, in an indirect sandwich assay, the particle includes a plurality of molecules of one of more compounds which are reactive with both the analyte and the tracer whereby a plurality of tracer molecules may be bound to each particle which is bound to the analyte. The compound on the particle which is bound to the analyte may be the same as or different from the compound on the particle which is bound to the tracer. Thus, in the assay, a single analyte molecule may be bound to a particle through a compound on the particle and a plurality of tracer molecules may be bound to such particle through remaining molecules on the particle, whereby in the assay a plurality of tracer molecules may be bound to a single analyte molecule through the particle bound to the analyte to thereby amplify the detectable label signal.

Thus, in the assay, there may be formed a complex of (i) binder; (ii) analyte bound to the binder; (iii) a particle containing a plurality of molecules of one or more compounds, at least one molecule of which is bound to the analyte; and (iv) a tracer bound to all or a portion of remaining molecules of at least one of the compounds on the particle. The tracer is comprised of a labeled binder for at least one of the compounds on the particle. Analyte may be determined or measured (qualitatively and/or quantitatively) by determining at least one of the tracer bound in the complex, or tracer, which during the assay, is not bound in the complex.

The compound or compounds on the particle may be (i) a coupled compound of a type hereinafter described comprised of a binder for the analyte and a ligand bound by the tracer; (ii) a whole antibody or fragment thereof (iii) a combination of a binder for the analyte and a ligand bound by the tracer (for example a combination of antibody and BSA or a combination of antibody and biotin); (iv) an immunoglobulin, etc.

The binder portion of the tracer is selected to bind to at least one of the compounds on the particle; e.g., if the compound(s) on the particle is a combination of antibody and BSA, the binder of the tracer may be anti-BSA; if the compound on the particle is an antibody, the binder of the tracer may be an antibody against the antibody on the particle or an antibody against a fragment thereof (anti-FC); if the compound on the particle is IgM, the binder of the tracer may be anti-IgM; if a compound on the particle is biotin, the binder of the tracer can be anti-biotin; etc.

In an indirect competition assay, the particle includes a plurality of molecules of one or more compounds with at least one compound being bound by the binder for the analyte used in the assay and the tracer, whereby a plurality of tracer molecules may be bound to each particle which is bound to the binder used in the assay. Thus, the particle contains at least one compound which is the analyte or appropriate analogue of the analyte and at least one compound which is bound by the tracer used in the assay. The compound bound by the tracer may be the same as or different from the compound on the particle which is bound by the assay binder. The term "appropriate analogue of the analyte" means that the analyte analogue is bound by the binder for the analyte.

Thus, in the indirect competition assay, there may be formed a complex of (i) a binder for the analyte; (ii) a particle containing a plurality of molecules of one or more compounds, at least one of which is bound to the binder for the analyte and (iii) a tracer bound to all or a portion of remaining molecules of at least one of the compounds on the: particle. The tracer is comprised of a labeled binder for at least one of the compounds on the particle. Analyte may be determined or measured (qualitatively and/or quantitatively) by determining at least one of tracer bound in the complex, or tracer which is not bound in the complex during the assay.

The compound or compounds on the particle may be (i) a coupled compound of a type hereinafter described comprised of a first ligand which is bound by the binder for the analyte and a second ligand which is bound by the tracer; (ii) analyte or appropriate analogue thereof; (iii) a combination of a ligand bound by the tracer (for example BSA or biotin) and analyte or appropriate analogue thereof, etc.

The binder portion of the tracer is selected to bind to at least one of the compounds on the particle; e.g., if the compound is a combination of analyte and BSA, the binder portion of the tracer may be anti-BSA; if the compound on the particle is the analyte (or appropriate analogue thereof) the binder portion of the tracer is a binder for the analyte, etc.

More particularly, in an embodiment of an indirect sandwich assay technique, in accordance with an aspect of the present invention, there is formed, in the assay, a complex of (i) binder; (ii) analyte bound to the binder; (iii) a particle containing a plurality of molecules of a coupled compound comprised of a binder for the analyte and a ligand, wherein, in the complex, coupled compound is bound to analyte; and (iv) tracer comprising a binder for the ligand of the coupled compound and a detectable label, wherein in the complex, tracer is bound to the coupled compound. Analyte may be determined or measured (qualitatively and/or quantitatively) by determining at least one of tracer bound in the complex, or tracer, which during the assay, is not bound in the complex.

In accordance with an embodiment of an aspect of the present invention wherein analyte is determined by an indirect competition assay, in the assay, there is formed a complex of (i) binder for the analyte; (ii) a particle derivatized with a plurality of molecules of a coupled compound comprised of a first ligand which is bound by the binder for the analyte and a second ligand, wherein, in the complex, coupled compound is bound to the binder; and (iii) tracer comprised of a binder for the second ligand of the coupled compound and a detectable label or marker, wherein in the complex, tracer is bound to the coupled compound. In the assay, analyte may be determined or measured (qualitatively and/or quantitatively) by determining at least one of tracer bound in the complex, or tracer, which during the assay, is not bound in the complex.

In accordance with an embodiment of the present invention, the particles are derivatized with a combination of compounds, one of which is a binder for the analyte and the other of which is bound by a ligand of the tracer.

In the assay, analyte may be determined or measured (qualitatively and/or quantitatively) by determining at least the tracer bound in the complex.

Thus, in accordance with the present invention, there is provided an amplification of signal in that the particle includes a plurality of molecules of at least one compound; accordingly, for each molecule of the at least one compound bound to analyte or binder in the complex, there is a plurality of tracer molecules linked thereto through the particle.

Thus, for example, in the indirect sandwich assay technique, a plurality of tracer molecules may be indirectly bound to a single analyte molecule in the complex, whereby there is provided an amplification of signal, which increases overall assay sensitivity.

The particle which is employed in conjunction with the compound(s) may be any one of a wide variety of particles which is capable of supporting a plurality of molecules of the compound(s), such as latex particles, sacs, etc.

The particle is preferably a sac, which may be any one of a wide variety of sacs, including but not limited to liposomes (single wall or multiple multilamellar), sometimes called vesicles or lipid vesicles; polymer microcapsules (for example, those made by coascervation), etc.

In accordance with a preferred embodiment, the detectable label employed in producing the tracer is comprised of a sac including a detectable marker or label. The sac employed with the at least one compound as a particle may be the same as or different from the sac used in formulating the tracer.

As known in the art, liposomes can be prepared from a wide variety of lipids, including phospholipids, glycolipids, steroids, relatively long chain alkyl esters; e.g., alkyl phosphates, fatty acid esters, lecithin, fatty amines and the like. A mixture of fatty materials may be employed, such as a combination of neutral steroid, a charged amphiphile and a phospholipid. As illustrative examples of phospholipids, there may be mentioned lecithin, sphingomyelin, dipalmitoyl lecithin, and the like. As representative steroids, there may be mentioned cholesterol, cholestanol, lanesterol, and the like. As representative examples of charged amphiphilic compounds, which generally contain from 12 to 30 carbon atoms, there may be mentioned mono- or dialkyl phosphate ester or an alkylamine; e.g., dicetyl phosphate, stearyl amine, hexadecyl amine, dilauryl phosphate, and the like.

Further details with respect to the preparation of liposomes are set forth in U.S. Pat. No. 4,342,826 and PCT International Publication No. WO80/OI515, both of which are hereby incorporated by reference.

In the case where the vesicle or liposome is also to include a detectable marker, the liposome may be prepared in an aqueous solution, including the detectable marker, whereby the liposome will include the marker in the interior thereof.

The sac or liposome, may be derivatized with the at least one compound, or in the case where the sac or liposome is employed in formulating the tracer, the sac or liposome may be derivatized with the appropriate binder for the at least one compound on the particle, by procedures known in the art. Such procedures include: covalent coupling, activation, etc. The sac or liposome may be derivitized with the at least one compound or binder after formation thereof, or in the alternative, a material to be employed in producing the sac may be derivatized with the at least one compound or the binder portion of the tracer, and such compound then formulated into a sac.

As hereinabove indicated, although a sac is preferred as the particle which is derivatized with at least one compound other solid particles may be derivatized with the at least one compound by procedures known in the art, such as adsorption, covalent coupling, activation, etc.

As hereinabove indicated, in such procedures, the particle is derivatized with a plurality of molecules of the at least one compound whereby a plurality of tracer molecules may be bound to each derivatized particle.

The coupled compound which is employed in an aspect of the assay of the present invention is comprised of two compounds, and the selection of the compounds is dependent upon the assay format. In a sandwich assay format, the coupled compound is comprised of a binder for the analyte, which is generally an antibody against the analyte (polyclonal and/or monoclonal), and a ligand for which there is a binder. In a case where the assay format is a competitive assay format, the coupled compound is comprised of a first ligand which is bound by the binder for the analyte, which first ligand may be either the analyte or appropriate analogue thereof, and a second ligand for which there is a binder.

The ligand portion of the coupled compound which is to be bound to the tracer may be any one of a variety of ligands for which a binder exists. Thus, for example, the ligand of the coupled compound which is to be bound to the tracer may be biotin, dinitrophenol, trinitrophenol, fluorescein, ferritin, peroxidase, albumin, etc. The ligand portion of the coupled compound which is to be bound to the tracer is generally a hapten.

The coupled compound may be produced by conjugating the two compounds to be used in forming the coupled compound by procedures known in the art; for example, by use of an appropriate coupling or spacer compound having two reactive functional groups; direct coupling by coupling a reactive functional group of one compound with a reactive functional group of a second compound, etc. A selection of an appropriate procedure is deemed to be within the scope of those skilled in the art from the teachings herein.

The coupled compound may be employed for derivatizing a particle, as hereinabove described. Alternatively, one of the compounds employed for producing the coupled compound may be used for derivatizing a particle, such as a sac, and thereafter the second compound coupled thereto.

These and other procedures should be apparent to those skilled in the art from the teachings herein.

In one embodiment, the particle is a liposome and the liposome is formulated to include a maleimido group for chemical attachment of an antibody through a sulfhydryl group as well as a liposome forming compound derivatized with biotin. Thus, for example, the liposome may be formulated to include both distearoyl phosphatidylethanolamine-maleimido and phosphatidyl-N-biotin ethanolamine. An antibody for the analyte may be conjugated to the liposome through the maleimido group and the tracer is comprised of labeled anti-biotin whereby in an assay, tracer is bound to the liposomes which are bound to analyte by the antibody conjugated to the liposomes.

The liposomes which include both antibody against the analyte and biotin may or may not include a detectable marker.

Thus, in an assay employing a "hybrid liposome" (liposome including conjugated antibody and conjugated biotin) the tracer may be a liposome having anti-biotin attached thereto (coating or conjugation) with the tracer liposome including a detectable marker. In the assay, a plurality of tracer liposomes are bound to the "hybrid liposome" which is bound to the analyte which amplifies the signal and increases assay sensitivity. The hybrid liposome may also include a detectable marker.

The detectable label or marker employed in producing the tracer may be any one of a wide variety of such markers, including, but not limited to radioactive labels, enzyme labels, chromogens (absorbing and/or fluorescent dyes), spin labels, magnetic labels, etc. The selection of a particular label is deemed to be within the scope of those skilled in the art from the teachings herein. As hereinabove indicated, a preferred detectable label for the tracer is a sac which includes a detectable label or marker, which may be an enzyme, chromogen, etc. As hereinafter indicated, a preferred detectable label or marker is a visible particulate label.

The binder for the analyte which is used in the indirect assay is dependent upon the analyte. Thus, for example, if the analyte is a hapten or an antigen, the binder may be an antibody (a polyclonal or monoclonal antibody), or a naturally occurring binder. If the analyte is an antibody, then the binder may be either an antigen which is recognized by the antibody or an antibody raised against the antibody analyte, which antibody may be either a monoclonal or polyclonal antibody or fragment thereof. The selection of a suitable binder for use in the assay is deemed to be within the scope of those skilled in the art from teachings herein.

In accordance with a preferred embodiment, the indirect assay is a solid phase assay wherein the binder is supported on a suitable solid support. Such solid supports are generally known in the art, and may take a wide variety of forms, such as a tube, a membrane, a sheet, a tray, a solid particle, etc. The selection of a suitable solid support is deemed to be within the scope of those skilled in the art from the teachings herein. Similarly, such solid supports may be formed from a variety of materials, and the binder may be supported on such supports by various techniques, such as adsorption, covalent coupling, etc.

In the sandwich assay, the complex may be formed by a variety of assay format techniques, including the so called "forward" "reverse" and "simultaneous" assay formats in the forward assay format, the solid support is initially contacted with the sample containing or suspected of containing the analyte, followed by contacting of the bound analyte with the particle and then with tracer.

In a reverse format, the analyte and particles including at least one compound, with or without tracer, may be initially contacted with each other, followed by contacting of the resulting complex with supported binder. If the tracer has not been previously employed, the tracer is then added to the complex which is previously formed, and which is comprised of binder-analyte-at least one compound (for example a coupled compound) supported on a solid particle.

In the indirect competitive assay, a binder for the analyte, which may be supported on a solid support, may be simultaneously contacted with the sample containing or suspected of containing the analyte, and a plurality of molecules of at least one compound supported on a particle, followed by addition of a tracer. Alternatively, sample, the particle and tracer may be simultaneously contacted with the binder.

These and other formats should be apparent to those skilled within the art from the teachings herein.

The amount and/or presence of analyte in the sample may then be determined by determining the tracer which is bound in the complex and/or the tracer which is not bound in the complex during the assay. In a quantitative determination, the amount of analyte may be determined by comparing the determined amount of tracer with a standard curve previously produced by effecting the assay with known quantities of analyte.

In accordance with a particularly preferred embodiment, the tracer employed in the indirect assay is labeled with a visible particulate label, and at least a portion of the solid support on which the binder for the analyte is supported has a surface area (area to unit weight of material) such that the binder can be supported on the test area in a concentration (weight to unit area) such that the tracer is visible under the assay conditions. The term "visible" as used herein means that the label can be seen without the use of instrumentation; i.e., with the naked eye. Such assay will be sometimes referred to herein as a "visible indirect assay" or "visible assay".

The test area which is employed in the visible assay is generally formed from a cellulose ester with nitrocellulose giving exceptionally good results. It is to be understood that the term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Such solid supports which are formed from cellulose esterified with nitric acid alone, or a mixture of nitric acid and another acid such as acetic acid, are often referred to as nitrocellulose paper.

Although nitrocellulose is a preferred material for the test area, it is to be understood that other materials, having a surface area sufficient for supporting the binder in a concentration as hereinabove described may also be employed for such test areas.

In general, the test area which is used in the visible assay has a surface area such that it is capable of supporting binder in a concentration of at least 1 ug/cm$^2$, (most generally in a concentration of at least 10 ug/cm$^2$) and preferably at least 40 ug/cm$^2$.

Thus, in accordance with an aspect of the present invention, there is provided a sandwich assay in which a sandwich is formed comprised of: support-binder-analyte-a plurality of molecules of at least one compound supported on a particulate support-tracer, wherein the particle includes at least one compound which is a binder for the analyte and at least one compound which is bound by the tracer.

As hereinabove indicated, in producing the tracer for the visible assay the binder for at least one compound on the particle is labeled with a particulate label, which is visible. A preferred particulate label is a sac of the type hereinabove described, which includes a dye or other colored substance as a marker, whereby the tracer, when used in the assay, is visible without destruction of the sac to release the colored substance.

The tracer comprised of a binder for at least one compound on the particle and a visible particulate label may also be produced by labeling the binder with an aqueous dispersion of a hydrophobic dye or pigment, or a polymer nucleus coated with such a dye or pigment. Such labels are described in more detail in U.S. Pat. No. 4,373,932, which issued on Feb. 15, 1983. The tracers produced in accordance with such patent may also be employed as tracers in the present invention.

As indicated in the aforesaid patent, the colored organic compounds which are used as labels are in the form of a hydrophobic sol, which hydrophobic organic dyes or pigments are insoluble in water or soluble only to a very limited extent. As indicated in the patent, particles of the aqueous dispersion of a hydrophobic dye or pigment, or of polymeric nuclei coated with such a dye or pigment have a particle size of at least 5 nm, and preferably from 10 to 500 nm.

Such tracers which are labeled with the hydrophobic dye or pigment or with polymeric nuclei coated with such dye or pigment, are visible tracers when used in the assay in accordance with the present invention.

The visible particulate label may be visible polymer particles, such as colored polystyrene particles, preferably of spherical shape.

As representative examples of other visible particulate labels which may be employed in producing a tracer for use in the assay of the present invention, in which the tracer would be visible, there may be mentioned: ferritin, phycoerythrins or other phycobili-proteins; precipitated or insoluble metals or alloys; fungal, algal, or bacterial pigments or derivatives such as bacterial chlorophylis; plant materials or derivatives, and the like.

The binder for the at least one compound on the particle may be labeled with the particulate label so as to produce a tracer for use in the invention by procedures generally known in the art, with the procedure which is used being dependent upon the binder and the particulate label which is employed. Such techniques include, covalent coupling, derivatization or activation, and the like. In producing a tracer wherein the binder is labeled with a sac, the sac may be produced from a component which has been derivatized with a binder, whereby the sac, when produced, is sensitized with the binder. In another procedure, the sac including the marker may be initially formed, followed by sensitizing the sac with binder by procedures known in the art.

Thus, in the visible assay the tracer is comprised of a binder for at least one compound on the particle and a particulate label (solid or solid-like, as opposed to non-solid labels, such as radioisotopes, enzymes and various fluorescent materials), and the particulate label provides a tracer which is visible under the assay conditions so that the presence and/or amount of analyte may be determined without further treatment and without the use of instrumentation; e.g., by use of a liposome containing a dye as the particulate label.

In accordance with a preferred aspect of the present invention, the binder for the analyte which is supported on the test area of the test substrate is preferably in a defined area of such test area such as, for example, in the form of a spot, rather than being dispersed over the entire test area of the test substrate. As hereinabove indicated, in accordance with a preferred embodiment, the binder for the analyte supported on the test area is preferably present in at least one microgram per $cm^2$, most generally at least 10 micrograms per $cm^2$, and preferably 40 micrograms per $cm^2$. The residual binding capacity of the test area of the overall test substrate may be saturated or blocked by treatment of the test area with one or more types of proteins which do not specifically bind materials to be employed in the assay. Thus, for example, residual binding capacity may be blocked by use of bovine serum albumin.

In some cases, in applying the binder for the analyte (in particular an antibody) to the test area, a polyhydroxy compound (glycerol, erythritol, sorbitol, etc.) or a sugar (glucose, sucrose, etc.) is included in the antibody solution to prevent non-specific binding (false positives) during the assay.

In accordance with a preferred embodiment, the test substrate includes a test layer having the test area for supporting the binder for the analyte in a concentration whereby the tracer used in the assay, when bound to the test area, under assay conditions is visible in the test area, without further treatment and also includes a flow controlling layer, beneath the test layer, which is formed of a porous material having a pore size to control the rate of flow of assay reagents through the test substrate, when such reagents are applied to the first layer. The test substrate also preferably includes a porous spacer layer for spacing an absorbent layer, formed of an absorbent material, from the flow controlling layer.

The absorbent layer has an absorbency sufficient to absorb the reagent liquids applied to the test layer during the assay. In addition, the absorbent materials functions to provide for flow through the test substrate.

It is to be understood that the entire test layer may be formed of the test area material or, alternatively, only the test area of the test layer may be formed of such a material.

In addition, since the test substrate is employed in a manner such that the assay reagents flow through the layers of the test substrate, the test area has a pore size which is greater than the size of the particulate label employed in the assay so that portions of the tracer, which do not become bound under assay conditions, flow into the test substrate and are not visible in the test area. In general, the test area should have a pore size which is at least 3 um, and most preferably at least 5 um. In general, the pore size does not exceed 12 um. It is to be understood, however, that although the previously described pore sizes are preferred, other pore sizes may be employed, depending upon the materials used in the assay.

The flow control layer of the test substrate is formed of a porous material which is employed to control the rate of flow of assay reagents through the test area and into the test substrate. The porous material which is employed in forming the flow control layer has a pore size which is less than the pore size of the material employed for forming the test area. Thus, in effect, the flow control layer functions to reduce the rate of flow of assay reagents through the more porous test area.

In general, the flow control layer, which functions to control the rate of flow of assay reagents through the test area and into the test substrate has a pore size of at least 0.5 micron, and in general does not have a pore size in excess of 10 microns.

The pore size of the flow control layer, as well as the thickness of the flow control layer are preferably controlled in a manner such that the flow of assay reagents through the test area provides the requisite sensitivity as well as a rapid and accurate assay.

The pore size and corresponding rate of flow selected for the second layer is dependent upon the expected range of analyte concentration. As the expected range of analyte concentration increases, the pore size and flow rate may increase. In fact, for some analytes which may be present in high concentrations, the second layer of the substrate may be omitted.

In accordance with one embodiment, the layer for controlling rate of flow through the test substrate is dimensioned and sized in a manner such that the flow rate of materials through the test area is in the order of at least 0.5 ml/min, and generally no more than 2 ml/min. It is to be understood, however, that the scope of the present invention is not limited to such flow rates.

The flow control layer is preferably formed from a non-fibrous material and preferably has pores or channels that provide for unidirectional flow from the test layer to the layer beneath the flow control layer; i.e., the flow control layer has defined flow channels which directs flow through the layer and minimizes flow across the layer. The pores or channels preferably are of uniform size. The flow control layer is preferably formed from a polycarbonate.

Immediately, below the flow control layer of the test substrate, there is provided a spacer layer of porous material which functions as a spacer between the flow controlling layer, and a porous absorbent layer. The spacer layer primarily functions to prevent materials which have passed through the top layers of the test substrate and into the absorbent layer of the test substrate from backing up into the top layers. To this end, the porous layer, which functions as a spacer, has a thickness which is sufficient to prevent materials which have passed into the absorbent layer from flowing back up into the top layers under assay conditions. In addition, the porous spacer layer has a pore size greater than the pore size of the flow controlling layer so that the spacer layer does not function to restrict flow through the test substrate.

It is to be understood, however, that in some cases, it may be possible to eliminate the spacer layer, provided that the characteristics of the remaining layers of the substrate; i.e., the test area, flow controlling layer and absorbent layer are such that the risk of material backing up into the test area from the absorbent layer is essentially eliminated. It is to be understood, however, that the use of a spacer layer is preferred. In the case where a flow control layer is not employed, the spacer layer spaces the test area from the absorbent layer.

The test substrate also includes an absorbent layer (fourth layer), which is a porous material which has an absorbing or absorbent capacity sufficient to absorb the liquid test reagents or materials which flow into the test substrate during the assay. The absorbent layer also functions to provide a driving force (concentration differential) which causes reagents applied to the test area to flow into the substrate; i.e., into the absorbent layer.

The materials which are employed in forming the various layers of the substrate are selected to have the hereinabove described characteristics. In addition, such materials should not produce non-specific binding of analyte or tracer. The materials may inherently have such characteristics, or alternatively, the materials may be treated to prevent nonspecific binding; for example, treatment with an appropriate protein, such as bovine serum albumin. The test area of the substrate is preferably also treated with a wetting agent in order to insure proper flow of the assay reagents through the test area and into the test substrate. As representative examples of wetting agents, there may be mentioned: sucrose, glycerol, glucose, sorbitol, etc. The test area may be simultaneously treated with a protein and wetting agent; e.g., an aqueous solution of BSA and sucrose.

Alternatively, the test substrate may be comprised of a test layer and an absorbent layer. These and other formats should be apparent to those skilled in the art from the teachings herein.

In general, the test substrate is supported on or in a suitable support, such as a card, or a container. The selection of a suitable support for the test substrate is deemed to be within the scope of those skilled in the art from the teachings herein.

In accordance with another aspect of the present invention, there is provided a test or reagent kit for determining analyte, which includes a binder for the analyte, particles derivatized with a plurality of molecules of at least one compound of the type hereinabove described, and a tracer. In the test or reagent kit for an indirect sandwich assay, at least one compound on the particle is a binder for the analyte and at least one compound is bound by the tracer, which tracer is an appropriate binder labeled with a detectable label or marker. In a test or reagent kit for determining analyte by an indirect competition assay format, the particle includes at least one compound, which is bound by the binder for the analyte, and at least one compound which is bound by the tracer with the tracer being comprised of a binder labeled with a detectable label or marker.

The detectable label may be as hereinabove described, and may be a visible particle, as hereinabove described. Similarly, the binder for the analyte may be in supported or unsupported form, and when in its supported form, it may be supported on any of the wide variety of supports hereinabove described.

The test or reagent kit may further include other reagents, such as wash liquids, buffers, standards, and the like. In a preferred embodiment, the binder for the analyte is supported on a solid support.

In the assays and kits of the present invention, the solid particle (preferably a liposome), which is derivatized with one or more compounds, may also include a detectable label, which is preferably identical to the detectable label of the tracer. In this manner, there is obtained a further amplification of signal. Thus, for example, in a sandwich assay, a liposome including a chromogen may be derivatized with a coupled compound and the tracer may be comprised of a liposome derivatized with a binder for the coupled compound which includes the same chromogen. Thus, in the assay, a detectable signal is provided from both the derivatized particle and the tracer.

Although in a preferred embodiment, the assay is accomplished in a "flow through" format in which the binder is supported on an appropriate substrate and sample, particle and tracer are caused to flow through the substrate, it is possible to employ other assay formats, e.g., contacting the supported binder without causing the reagents to flow through the substrate, such as use of a text card, or a chromatographic or capillary flow over the surface of the test substrate, etc.

Similarly, although it is preferred to employ a test substrate of the configuration hereinabove described when using a flow through assay, it is possible to use other configurations; e.g., a combination of test substrate and absorbent material without the flow control and spacer layers.

The indirect sandwich assay may be accomplished in a variety of formats.

For example, the analyte and particle may be contacted with each other and the resulting mixture contacted with the supported binder. As a further alternative, it may be possible to contact tracer, particle and sample, and the resulting mixture contacted with the supported binder.

As a further alternative within the spirit and scope of the present invention, it is possible to employ an indirect sandwich assay technique in an assay format other than a visible assay format, wherein the tracer is comprised of a binder and a liposome including a detectable marker. Thus, for example, the detectable marker may be an enzyme, radioactive material, chromogen (fluorescent and/or absorbing dye), etc.

In such a modification the solid support for the supported binder may take the form of a tube, particulate support, sheet, membrane, filter, etc. The assay may be accomplished in a flow through format (assay reagents flow through a support containing the binder) or may be a "batch" type of assay; for example incubation in a tube, tray, etc. The analyte may be determined by determining the tracer in the bound phase (complex) and/or in the unbound phase.

The present invention is applicable to procedures and products for determining a wide variety of analytes. As representative examples of types of analytes, there may be mentioned: drugs, including therapeutic drugs and drugs of abuse; hormones, vitamins, proteins, including antibodies of all classes; peptides; steroids; bacteria; fungi; viruses; parasites; components or products of bacteria, fungi, viruses, or parasites; allergens of all types; products or components of normal or malignant cells; etc. As particular examples, there may be mentioned $T_4$; $T_3$; digoxin; hcG; insulin; theophylline; luteinizing hormone; organisms causing or associated with various disease states, such as HIV, streptococcus pyogenes (group A), Herpes Simplex I and II, *cytomegalovirus, rubella, chlamydiae, Candida albicans, Neisseria gonorrhoeae, Hemophilus influenzae*, Group B Strep, *S. pneumoniae, Neisseria meningitidis, Clostridium difficile*, antibodies specific for organisms e.g. Rubella specific antibody HTLV III(HIV) specific antibody, etc.

The analyte may be determined in various samples, including for example, body fluids, such as saliva, urine, serum; swab samples; e.g., from the throat etc. In some cases, it may be possible to detect analyte in whole blood.

The invention will be further described with reference to the following examples; however, the scope of the invention is not to be limited thereby:

EXAMPLE I

Biotinylation of monoclonal antibody (MAb 22B9) against *Neisseria meningitidis* Group B.

(i) Antibody was dialyzed against 10 mM Na phosphate buffer pH 7.4 containing 0.15M NaCl. After dialysis the concentration of antibody was adjusted to 1 mg/ml and the pH was adjusted to 5.5 by the addition of 1M acetate buffer pH 4.5.

(ii) Sodium periodate (100 mM in 20 mM sodium acetate/ 0.15M NaCl pH 5.5) was added to the solution of antibody to a final concentration of 10 M. Oxidation was allowed to continue for 15–30 min at room temperature, after which time the reaction was quenched by the addition of ethylene glycol (to 0.1M). (iii) The antibody solution was passed down a G-25 column equilibrated with 20 mM acetate/0.15M NaCl pH 5.5. Fractions containing antibody were pooled. (iv) Biotin hydrazide (Approximately 5 mg/ml in DMSO) was added to the pooled antibody such that the final concentration of biotin hydrazide was 0.25 mg/ml. The antibody concentration at this step was 0.3–0.5 mg/ml. The mixture was allowed to stand for 24 hours at 4° C. and was then dialyzed against 0.1M NaHCO₃\pH 8.3 to remove unbound biotin hydrazide.

EXAMPLE II

Detection of capsular polysaccharide of *N. meningitidis* Group B.

step (i) Monoclonal antibody (MAb 22B9) against capsular polysaccharide of NmB was spotted on 5 um nitrocellulose—0.5 ul spotted at 500 ug/ml. The membrane was allowed to dry for 15 min at room temperature.

step (ii) The spotted membrane was then blocked by incubation in PBS containing 0.5% (w/v)low fat dried milk for 60 min at 37° C.

step(iii) The blocked membrane was washed with PBS to remove excess blocking solution and allowed to dry at room temperature.

step (v) The membrane was then placed on absorbent paper.

step (v) Capsular polysaccharide of NmB (volume 200 ul) was then passed through the membrane. A fraction of the antigen was captured by the spotted MAb 22B9.

step (vi) A solution containing liposomes coated with biotinylated MAb 22B9 was then passed through the membrane (volume of solution was 200 ul). These liposomes, which contained sulforhodamine B, bound to the captured antigen and provided a faint signal.

step (vii) A solution containing liposomes coated with goat anti-biotin antibody was then passed through the membrane (volume 100 ul). These liposomes, which also contained sulforhodamine B, bound to the liposomes which had been captured in step (vi) and increased the intensity of the signal.

step (viii) Buffer (200 ul) was passed through the membrane to wash out unattached liposomes.

The present invention is particularly advantageous in that the sensitivity of the assay is improved by using derivatized particle and tracer to detect analyte. In addition, it is possible to use one tracer for assays for different analytes. The sensitivity of the assay may be increased by amplifying the signal; i.e., a plurality of tracer molecules are bound indirectly to a single analyte molecule in the sandwich assay format.

EXAMPLE III

I . ASSAY USING HYBRID LIPOSOMES:

A. Preparation of Biotin/Maleimido Liposomes

Biotin/Maleimido liposomes containing sulforhodamine B were prepared as described in U.S. Pat. No. 4,920,046, with the following modification:

1 mg of phosphatidyl N-biotinethanolamine (Avanti Polar Lipids 831168) was added to:

a. 50 mg cholesterol (Sigma CH-PL), b. 94 mg distearoyl phosphatidyl choline, (Avanti Polar Lipids 850365), c. 10 mg distearoyl phosphatidyl glycerol (Avanti Polar Lipids), d. 3.75 mg crosslinking agent (distearoyl phosphatidyl ethanol-amine-p-maleimidophenyl) capryl (BD Immunodiagnostics, Orangeburg, N.Y.) ; and e. 50 ml chloroform (Fisher).

The biotin/maleimido liposomes prepared according to U.S. Pat. No. 4,920,046 thus contained both biotin and reactive maleimide groups attached to the lipid bilayer.

B. Coupling of Analyte Specific Antibody to Biotin/Maleimido Liposomes

1. Affinity purified antibody to the capsular polysaccharide of *Hemophilus influenzae* was dialyzed against phosphate buffered saline (100 mM sodium phosphate, 150 mM sodium chloride, pH 7.4). Antibody concentration after dialysis was 0.9 mg/ml and volume of antibody solution was 1.35 ml.

2. The antibody solution was adjusted to pH 6.6 by addition of acetate solution (pH 4.5).

A solution of PBS/25 mMEDTA (1/10th volume of antibody solution) was added to the antibody solution.

A solution of DTT (1M) was added to give a final concentration of DTT of 50 mM.

The antibody/DTT mixture was allowed to sit for 60 minutes at room temperature.

DTT was removed from the reduced antibody by passing the reaction mixture over a column of Sephadex G-25 equilibrated with Tris buffered saline (50 mM Tris, 50 mM sodium acetate, 50 mM sodium chloride, 1mMEDTA, pH 8.0). Antibody was collected and pooled. Antibody and biotin/maleimido liposomes were mixed in the ratio of 0.5 mg of antibody per 80 µmol of phosphorus. The pH of the antibody/hybrid liposome mixture was adjusted to PH 8.0 by addition of 1M Tris base. The coupling of antibody was allowed to continue overnight.

Unreacted antibody was removed from liposomes by pelleting the liposomes and resuspending in Tris buffer [20 mM Tris, 20 mM MEDTA, 2% (w/v) glycerol, 0.05% (v/v) DMSO, 0.02% (w/v) sodium azide, pH 6.7]. Reacted liposomes were stored at 4° C.

C. Coupling of Rabbit Anti-Biotin Antibody to Liposomes

1. Affinity purified rabbit anti-biotin antibody was dialyzed against phosphate buffered saline.

2. Rabbit anti-biotin antibody was coupled to sulphorhodamine B containing liposomes by the procedure described in the previous section (B) with the following modifications:
   a. The ratio of anti-biotin antibody to liposomes was 1.5 mg antibody per 80 µmol of phosphorus, and
   b. Liposomes did not contain biotin phosphatidylethanolamine. The sulforhodamine B containing liposomes were prepared according to the procedure described in U.S. Pat. No. 4,920,046.

D. Assay Procedure Using Hybrid Liposomes and Rabbit Anti-Biotin Coupled Liposomes 1. Affinity purified rabbit antibody specific for capsular polysaccharide of *H. influenzae* (0.23 mg/ml, 0.5 µl) was spotted on nitrocellulose.

2. The spotted membrane was dried for 30 minutes a 37° C.

3. The membrane was blocked by a solution of 0.5% non fat dried milk (Blotto) in phosphate buffered saline.

4. The membrane was then placed on absorbent paper.

5. Capsular polysaccharide of *H. influenzae* (volume 200 µl) was then passed through the membrane. A fraction of the polysaccharide antigen was captured by the spotted antibody.

6. A suspension of liposomes (volume 200 µl) was then passed through the membrane. These liposomes contained biotin phosphatidylethanolamine in the lipid bilayer and rabbit antibody specific for the capsular polysaccharide of *H. influenzae* also attached to the lipid bilayer. The preparation of these liposomes was described in Sections A and B of Example III.

7. The membrane was then washed by passage of phosphate buffered saline (100–200 µl).

8. The signal was amplified by passing a suspension of liposomes coated with rabbit anti-biotin antibody through the membrane. The volume of liposomes used at this step was usually 150 µl. These liposomes also contained sulforhodamine B and were prepared as described in Section C of Example III.

9. The membrane was washed by passage of PBS (100–200 µl) through the membrane. Endpoint sensitivity using the two liposome format (hybrid liposome/rabbit anti-biotin liposome) was 0.24–0.49 ng *H. influenzae* polysaccharide/ml. In contrast, endpoint sensitivity with a single liposome format (i.e., steps 1–7 of Section D, Example III) was 7.8 ng polysaccharide/ml. Thus, the two liposome format of Example III gave 8–16 fold improvement in sensitivity over the single liposome format.

These and other advantages should be apparent to those skilled in the art from the teachings herein.

Numerous modifications and variations of the present invention are possible in light of the above, and therefore, within the scope of the appended claims, the invention may be practiced otherwise than as particularly described.

What is claimed is:

1. An indirect sandwich assay process for determining analyte, comprising:

(a) forming in the assay a complex of (i) solid phase bound first specific binding partner for the analyte; (ii) analyte; (iii) a primary particle having attached to the exterior thereof directly or through linking groups multiple first specific binding partners and a plurality of molecules specific for a second specific binding partner attached to a tracer particle as in (iv) wherein each molecule specifically binds to each second specific binding partner attached to the tracer particle; and (iv) the tracer particle comprising a secondary detectably labeled particle having attached to the exterior thereof a second specific binding partner for the plurality of molecules of (iii), wherein said complex is formed by contacting the solid phase bound first specific binding partner of (i) with the analyte of (ii), the primary particle of (iii) and the tracer particle of (iv), either by contacting:

(1) a complex of the solid phase bound first specific binding partner of (i) and the analyte of (ii) with the primary particle of (iii) and subsequently contacting the complex resulting therefrom with the tracer particle of (iv), or (2) a complex of the analyte of (ii) and the primary particle of (iii) with the solid phase bound first specific binding partner of (i) and contacting the complex resulting therefrom with the tracer particle of (iv), or (3) a complex of the analyte of (ii), the primary particle of (iii) and the tracer particle of (iv) with the solid phase bound first specific binding partner of (i) and (b) determining analyte by determining bound or unbound tracer.

2. The process of claim 1 wherein a coupled compound is attached to the exterior of said primary particle directly or through a linking group and comprises a first specific binding partner for the analyte and a molecule capable of binding to a second specific binding partner attached to the secondary particle.

3. The process of claim 1 wherein the secondary particle which has a detectable label therein is a liposome.

4. The process of claim 3 wherein the primary particle has a detectable label therein.

5. The process of claim 1 wherein the solid phase is nitrocellulose.

6. The process of claim 1 wherein the detectable label is a chromogen.

7. The process of claim 1 wherein the specific binding partner for the analyte is attached to the solid phase in a concentration of at least 1 µg/cm$^2$ and the label of the tracer particle is a visible particulate label.

8. The process of claim 1 wherein the first specific binding partner is an antibody, the molecule capable of binding to the second specific binding partner on the primary particle therewith is biotin or a specific binding analog thereof and the second specific binding partner, which is on the tracer particle, is antibiotin antibody or a specific binding analog thereof.

9. The process of claim 8 wherein the secondary particle which has a detectable label therein is a liposome.

10. The process of claim 1 wherein the molecule on the primary particle is a ligand, and the second specific binding partner on the tracer particle is an antibody for said ligand.

11. The process of claim 1 wherein the first specific binding partner and the molecule for the second specific binding partner are each independently conjugated to the primary particle.

12. The process of claim 11 wherein the tracer particle is comprised of a liposome having a detectable marker therein and anti-ligand attached to the exterior of said liposome.

13. The process of claim 12 wherein the ligand is biotin.

14. The process of claim 13 wherein the primary particle has therein a detectable label identical to the detectable label for the tracer particle.

15. The assay of claim 1 wherein the primary particle has a detectable label therein.

16. The process of claim 1 wherein the primary particle is a liposome.

17. An assay composition for determining analyte comprising: (i) a solid phase bound first specific binding partner for the analyte; (ii) at least one primary particle having attached to the exterior thereof directly or through linking groups multiple first specific binding partners and a plurality of molecules specific for a second specific binding partner attached to a tracer particle as in (iii), wherein each molecule specifically binds to each second specific binding partner attached to the tracer particle; and (iii) the tracer particle comprising a secondary detectably labeled particle having attached to the exterior thereof a second specific binding partner for the plurality of molecules of (ii).

18. The composition of claim 17 wherein a coupled compound is attached to the exterior of said primary particle directly or through a linking group and comprises a first specific binding partner for the analyte and a molecule capable of binding to a second specific binding partner attached to the secondary particle.

19. The composition of claim 18 wherein the secondary particle is a liposome.

20. The composition of claim 18 wherein the solid phase is nitrocellulose.

21. The composition of claim 18 wherein the specific binding partner for the analyte is attached to the solid phase in a concentration of at least 1 µg/cm$^2$ and the label of the tracer particle is a visible particulate label.

22. The composition of claim 18 wherein the primary particle having one or more compounds supported thereon has therein a detectable label identical to the detectable label of the tracer particle.

23. The composition of claim 17 wherein the secondary particle is a liposome.

24. The composition of claim 17 wherein the specific binding partner for the analyte is attached to the solid phase in a concentration of at least 1 µg/cm$^2$ and the label of the tracer particle is a visible particulate label.

25. The composition of claim 17 wherein the molecule on the primary particle is a ligand and the second specific binding partner on the tracer particle is an antibody for said ligand.

26. The composition of claim 25 wherein the tracer particle comprises a labeled anti-ligand antibody.

27. The composition of claim 26 wherein the tracer particle is comprised of a liposome having a detectable marker therein and a ligand specific binding partner attached to the exterior of said liposome.

28. The composition of claim 27 wherein the ligand is biotin.

29. The composition of claim 17 wherein the primary particle is a liposome.

30. An indirect competitive assay process for determining analyte, comprising:
(a) forming in the assay a complex of (i) a solid phase bound first specific binding partner for the analyte; (ii) a primary particle capable of binding to (i) having attached to the exterior thereof directly or through linking groups multiple analyte or analyte analog molecules and a plurality of molecules for a second specific binding partner attached to a tracer particle as in (iii), wherein each molecule specifically binds to each second specific binding partner attached to the tracer particle; and (iii) the tracer particle comprising a secondary detectably labeled particle having attached to the exterior thereof a second specific binding partner for the plurality of molecules of (ii), wherein said complex is formed by contacting the solid phase bound first specific binding partner of (i) with a sample containing analyte, the primary particle of (ii) and the tracer particle of (iii), either by
(1) simultaneously contacting the solid phase bound first specific binding partner of (i) with the sample, the primary particle of (ii), and the tracer particle of (iii), or
(2) simultaneously contacting the sample, the primary particle of (ii) and the tracer of particle of (iii) with the solid phase bound first specific binding partner of (i) and
(b) determining analyte by determining bound or unbound tracer.

31. An assay composition for determining analyte in a process as defined in claim 30, comprising: (i) a solid phase bound first specific binding partner for the analyte; (ii) a primary particle having attached to the exterior thereof directly or through linking groups multiple analyte or analyte analog molecules and a plurality of molecules for a second specific binding partner attached to a tracer particle as in (iii), wherein each molecule specifically binds to each second specific binding partner attached to the tracer particle; and (iii) the tracer particle comprising a secondary detectably labeled particle having attached to the exterior thereof a second specific binding partner for the plurality of molecules of (ii).

32. The composition of claim 31 wherein the secondary particle is a liposome.

33. The process of claim 30 wherein the secondary particle is a liposome.

* * * * *

UNITED STATES PATENT AND TRADEMARK OFFICE
CERTIFICATE OF CORRECTION

PATENT NO. : 5,567,591

DATED : October 22, 1996

INVENTOR(S): Stepher J. Lovell; and Jeffrey H. Bruton

It is certified that error appears in the above-identified patent and that said Letters Patent is hereby corrected as shown below:
Column 11, Line 48,
"10 M" should read -- 10mM --.

Signed and Sealed this

Twenty-eighth Day of January, 1997

Attest:

BRUCE LEHMAN

Attesting Officer    Commissioner of Patents and Trademarks